US007194292B2

(12) United States Patent
Norris

(10) Patent No.: US 7,194,292 B2
(45) Date of Patent: Mar. 20, 2007

(54) SIMULTANEOUS SIGNAL ATTENUATION MEASUREMENTS UTILIZING FREQUENCY ORTHOGONAL RANDOM CODES

(75) Inventor: Mark A. Norris, Louisville, CO (US)

(73) Assignee: General Electric Company, Schenectady, NY (US)

( * ) Notice: Subject to any disclaimer, the term of this patent is extended or adjusted under 35 U.S.C. 154(b) by 347 days.

(21) Appl. No.: 10/786,938

(22) Filed: Feb. 25, 2004

(65) Prior Publication Data

US 2005/0187451 A1 Aug. 25, 2005

(51) Int. Cl.
*A61B 5/00* (2006.01)
(52) U.S. Cl. .................... 600/323; 600/330; 600/336
(58) Field of Classification Search ............... 600/323, 600/330, 336
See application file for complete search history.

(56) References Cited

U.S. PATENT DOCUMENTS

| | | | |
|---|---|---|---|
| 4,800,885 A | 1/1989 | Johnson ................... 128/633 |
| 4,819,752 A | 4/1989 | Zelin ....................... 128/633 |
| 4,848,901 A | 7/1989 | Hood, Jr. .................. 356/41 |
| 4,930,140 A | 5/1990 | Cripps et al. ............... 375/1 |
| 4,972,331 A | 11/1990 | Chance ................... 364/550 |
| 5,122,974 A | 6/1992 | Chance ................... 364/550 |
| 5,193,543 A | 3/1993 | Yelderman ............... 128/633 |
| 5,204,874 A | 4/1993 | Falconer et al. ............ 375/1 |
| 5,277,181 A | 1/1994 | Mendelson et al. ....... 128/633 |
| 5,320,098 A | 6/1994 | Davidson ................. 128/630 |
| 5,343,818 A | 9/1994 | McCarthy et al. ....... 128/633 |
| 5,349,952 A | 9/1994 | McCarthy et al. ....... 128/633 |
| 5,349,953 A | 9/1994 | McCarthy et al. ....... 128/633 |
| 5,387,259 A | 2/1995 | Davidson ................. 128/630 |
| 5,460,182 A | 10/1995 | Goodman et al. ........ 128/664 |
| 5,766,127 A | 6/1998 | Pologe et al. ............ 600/310 |
| 5,769,791 A | 6/1998 | Benaron et al. .......... 600/473 |
| 5,772,597 A | 6/1998 | Goldberger et al. ...... 600/473 |
| 5,774,213 A | 6/1998 | Trebino et al. .......... 356/320 |
| 5,782,758 A | 7/1998 | Ausec et al. ............. 600/336 |
| 5,785,658 A | 7/1998 | Benaron et al. .......... 600/473 |
| 5,800,348 A | 9/1998 | Kaestle .................... 600/322 |
| 5,805,583 A | 9/1998 | Rakib ...................... 370/342 |
| 5,807,261 A | 9/1998 | Benaron et al. .......... 600/473 |
| 5,891,022 A | 4/1999 | Pologe ..................... 600/323 |
| 5,891,024 A | 4/1999 | Jarman et al. ............ 600/323 |
| 5,919,134 A | 7/1999 | Diab ........................ 600/323 |
| 5,921,921 A | 7/1999 | Potratz et al. ............ 600/323 |
| 5,934,277 A | 8/1999 | Mortz ...................... 128/633 |
| 5,995,858 A | 11/1999 | Kinast ..................... 600/323 |
| 6,097,712 A | 8/2000 | Secord et al. ............ 600/323 |
| 6,229,856 B1 | 5/2001 | Diab et al. ............... 375/316 |
| 6,269,267 B1 | 7/2001 | Brady et al. .............. 607/5 |

(Continued)

*Primary Examiner*—Eric F. Winakur
*Assistant Examiner*—Jack Lin
(74) *Attorney, Agent, or Firm*—Marsh Fischmann & Breyfogle LLP

(57) ABSTRACT

A method for use in operating a signal attenuation measurement device used to obtain a physiological parameter of a patient and an apparatus for use in determining at least one physiological parameter relating to a patient from at least first and second signals transmitted to a patient tissue site and attenuated thereby are provided. In accordance with the method and apparatus of the present invention, the first and second signals are multiplexed using frequency orthogonal code division multiplexed excitation waveforms. This allows for both relatively good source separation of the signals and whitening of external noise.

28 Claims, 7 Drawing Sheets

U.S. PATENT DOCUMENTS 6,505,133 B1 * 1/2003 Hanna et al. .................. 702/74
6,533,733 B1 * 3/2003 Ericson et al. .............. 600/561
6,650,918 B2 * 11/2003 Terry .......................... 600/336

* cited by examiner

SIMULTANEOUS SIGNAL ATTENUATION MEASUREMENTS UTILIZING FREQUENCY ORTHOGONAL RANDOM CODES

FIELD OF THE INVENTION

The present invention relates in general to simultaneous signal attenuation measurement systems and, in particular, to the use of combined multiplexing techniques in such systems to identify attenuation characteristics associated with individual signal components.

BACKGROUND OF THE INVENTION

Signal attenuation measurements generally involve transmitting a signal towards or through a medium under analysis, detecting the signal transmitted through or reflected by the medium and computing a parameter value for the medium based on attenuation of the signal by the medium. In simultaneous signal attenuation measurement systems, multiple signals are simultaneously transmitted (i.e., two or more signals are transmitted during at least one measurement interval) to the medium and detected in order to obtain information regarding the medium.

Such attenuation measurement systems are used in various applications in various industries. For example, in the medical or health care field, optical (i.e., visible spectrum or other wavelength) signals are utilized to monitor the composition of respiratory and anesthetic gases, and to analyze tissue or a blood sample with regard to oxygen saturation, analyte values (e.g., related to certain hemoglobins) or other composition related values.

The case of pulse oximetry is illustrative. Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's tissue site such as a finger, earlobe or nasal septum. The probe is used to transmit pulsed optical signals of at least two wavelengths, typically red and infrared, to the patient's tissue site. The different wavelengths of light used are often referred to as the channels of the pulse oximeter (e.g., the red and infrared channels). The optical signals are attenuated by the patient tissue site and subsequently are received by a detector that provides an analog electrical output signal representative of the received optical signals. The attenuated optical signals as received by the detector are often referred to as the transmitted signals. By processing the electrical signal and analyzing transmitted signal values for each of the channels at different portions of a patient pulse cycle, information can be obtained regarding blood oxygen saturation or blood analyte values.

Such pulse oximeters generally include multiple sources (emitters) and one or more detectors. A modulation mechanism is generally used to allow the contribution of each source to the detector output to be determined. Some pulse oximeters employ time division multiplexing (TDM) signals. As noted above, the processing of the electrical signals involves separate consideration of the portions of the signal attributable to each of the sources. Such processing generally also involves consideration of a dark current present when neither source is in an "on" state. In TDM oximeters, the sources are pulsed at different times separated by dark periods. Because the first source "on" period, the second source "on" period and dark periods occur at separate times, the associated signal portions can be distinguished for processing.

Alternatively, some pulse oximeters may employ frequency division multiplexing (FDM) signals. In the case of FDM, each of the sources is pulsed at a different frequency resulting in detector signals that have multiple periodic components. Conventional signal processing components and techniques can be utilized to extract information about the different frequency components.

Another type of multiplexing that may be employed in pulse oximeters is code division multiplexing (CDM). In the case of CDM, each of the sources is pulsed in accordance with a unique code comprising a series of high (e.g., +1) and low (e.g., 0) values that identifies each channel from the other channel(s). The codes that are used generally have a number of preferred characteristics, including a random or pseudo-random pattern, orthogonality or near-orthogonality with respect to one another, a substantially equal number of high and low values within a particular code sequence, a relatively even distribution of high and low values within a particular code sequence, and a substantially even distribution of transitions between high and low values within a particular code sequence.

In order to accurately determine information regarding the subject, it is desirable to minimize noise in the detector signal. Such noise may arise from a variety of sources. For example, one source of noise relates to ambient light incident on the detector. Another source of noise is electronic noise generated by various oximeter components, as well as other electrical and electronic equipment within the vicinity of the pulse oximeter. Many significant sources of noise have a periodic component.

Various attempts to minimize the effects of such noise have been implemented in hardware or software. For example, various filtering techniques have been employed to filter from the detector signal frequency or wavelength components that are not of interest. However, because of the periodic nature of many sources of noise and the broad spectral effects of associated harmonics, the effectiveness of such filtering techniques is limited. In this regard, it is noted that both TDM signals and FDM signals are periodic in nature. Accordingly, it may be difficult for a filter to discriminate between signal components and noise components having a similar period. Furthermore, source signal separation can suffer when using CDM signals if there are post-calibration changes in the dynamics of the system. Such post-calibration changes are common given the typically different response rates of different detectors.

SUMMARY OF THE INVENTION

Accordingly, the present invention combines the beneficial aspects of two different multiplexing techniques, namely FDM and CDM, to overcome the aforementioned limitations of such techniques when used alone. Such combination achieves a number of advantages associated with each technique, including the relatively good source separation achieved with FDM techniques and the desirable whitening of external noise achieved with CDM techniques.

In accordance with one aspect of the present invention, a method for use in operating a signal attenuation measurement device is provided. Although it may be configured differently, the measurement device generally includes a source system for generating at least first and second signals and for transmitting the first and second signals to a patient tissue site that attenuates the signals, a detector system for receiving at least first and second attenuated signals from the patient tissue site corresponding with the first and second signals transmitted to the patient tissues site and for providing a composite detector signal based on the first and second attenuated signals, and a parameter estimation module for determining a physiological parameter regarding the patient based on information included in the detector signal. In one embodiment, the measurement device comprises a pulse oximeter. The physiological parameter may, for example, be a blood oxygen saturation value and/or a blood analyte value.

The method includes the step of operating the source system to multiplex the first and second signals in accordance with first and second frequency orthogonal code division multiplexed excitation waveforms or vectors. The detector signal is processed to provide a processed signal for demultiplexing that includes information regarding the first and second attenuated signals. The processed signal is demultiplexed using at least one demultiplexing signal that includes a series of values corresponding with one of the first and second frequency orthogonal code division multiplexed waveforms. The demultiplexing process yields demultiplexed information corresponding to each of the first and second attenuated signals. The demultiplexed information is usable by the parameter estimation module of the measurement device for determining the physiological parameter regarding the patient.

In accordance with the method of the present invention, the first frequency orthogonal code division multiplexed excitation waveform may be comprised of a number of first pattern groups comprised of randomly selected values (e.g., 0 or +1). Each randomly selected value in a first pattern group corresponds with one of a plurality of pulse patterns selected from a first set of pulse patterns. Likewise the second frequency orthogonal code division multiplexed excitation waveform may be comprised of a number of second pattern groups comprised of randomly selected values (e.g., 0 or +1). Each randomly selected value in a second pattern group corresponds with one of a plurality of pulse patterns selected from a second set of pulse patterns. In order to establish frequency orthogonality of the excitation waveforms, the number of first pattern groups in the first excitation waveform is preferably a prime number (e.g., 3) different from a prime number (e.g., 2) of second pattern groups in the second excitation waveform. In this regard, the first and second pattern groups generally include different appropriate numbers of randomly selected values (e.g., 4 and 6 values, respectively) to provide equal length excitation waveforms. In one embodiment of the method of the present invention, the first set of pulse patterns includes two different pulse patterns and the second set of pulse patterns includes two different pulse patterns. The pulse patterns within the first and second sets of pulse patterns may be different digital codes comprised of a equal length series of high (e.g., +1) and low (e.g., 0) values. Preferably, the high values in the pulse patterns from the first set of pulse patterns do not overlap in time with the high values from the pulse patterns in the second set of pulse patterns. Also, it is preferred that each of the pulse patterns within the first set of pulse patterns be substantially orthogonal to each of the pulse patterns within the second set of pulse patterns. The duty cycle may be less than 50%.

Typically the processed signal is an analog signal. In this regard, in the step of processing the detector signal, the detector signal, or an appropriate portion thereof, may be converted into a series of digital values. This allows for subsequent demultiplexing of the processed signal to be implemented digitally in, for example, a multi-purpose digital signal processor, an application specific integrated circuit (ASIC), a field programmable gate array (FPGA), or another type of digital hardware/software device. It is preferable when converting the analog detector signal to sample the detector signal multiple times within a time period corresponding to the high value and low value time periods of the first and second signals. Prior to converting the analog detector signal, it may be desirable to filter the detector signal to remove one or more selected frequency components. Once converted, the processed signal may be demultiplexed by processing the processed signal using a first demultiplexing signal including a series of values corresponding to the first frequency orthogonal code division multiplexed excitation waveform and also processing the processed signal using a second demultiplexing signal including a series of values corresponding to the second frequency orthogonal code division multiplexed excitation waveform signal. These demultiplexing signal series of values are synchronized with the excitation waveforms and demultiplexing may be accomplished by taking the bitwise product of the digitized detector signal and each of the demultiplexing signals.

According to another aspect of the present invention, an apparatus for use in determining at least one physiological parameter relating to a patient from at least first and second signals transmitted to a patient tissue site and attenuated thereby includes a source system, a detector system, and a signal processing device. The source system is operative to generate the first and second signals and to transmit the first and second signals to the patient tissue site. In this regard, the source system may include first and second light sources that are operative to transmit first and second light signals centered at first and second wavelengths, respectively, to the patient tissue site. The physiological parameter determined by the apparatus may, for example, be a blood oxygen saturation value and/or a blood analyte value. In this regard, the first wavelength may be within the infrared portion of the electromagnetic spectrum and the second wavelength may be within the red portion of the electromagnetic spectrum.

The detector system is operative to receive first and second attenuated signals from the patient tissue site. The first and second attenuated signals correspond with the first and second signals transmitted to the patient tissues site by the source system. Where the first and second signals transmitted by the source system are light signals the detector system may include a photo-detector. The detector system is further operative to provide a composite detector signal based on the first and second attenuated signals. In one embodiment of the apparatus of the present invention, the composite detector signal is an analog signal, and the detector system also includes an analog-to-digital converter that is operative to convert the detector signal, or a desired portion thereof, into a series of digital values. Preferably, the analog-to-digital converter samples the detector signal multiple times within a time period corresponding to one of a high value and a low value time period of the first and second signals. The detector system may also include an amplifier that is operative to amplify the detector signal and filter the detector signal to remove one or more selected frequency components before it is converted to a digital signal by the analog-to-digital converter.

The signal processing device of the apparatus includes both a code generation module and a demodulation module, which may be implemented in software executable by the processing device, in hardware included in the processing device, or in a combination of hardware and software. In this regard, the processing device may comprise, for example, multi-purpose digital signal processor, an ASIC, a FPGA, or another type of digital hardware/software device. The code generation module is operative to drive the source system to multiplex the first and second signals in accordance with first and second frequency orthogonal code division multiplexed excitation waveforms or vectors. The first and second frequency orthogonal code division multiplexed excitation waveforms may be configured as previously summarized in connection with the method of the present invention. The demodulation module is operative to demultiplex the composite detector signal using at least one demultiplexing signal (and preferably first and second demultiplexing signals) including a series of values corresponding with one of the first and second frequency orthogonal code division multiplexed waveforms. The composite detector signal is demultiplexed by the demodulation module to obtain demultiplexed information corresponding to each of the first and second attenuated signals. The demultiplexed information may be used by a parameter estimation module implemented in the processing device in determining the physiological parameter regarding the patient.

These and other aspects and advantages of the present invention will be apparent upon review of the following Detailed Description when taken in conjunction with the accompanying figures.

DESCRIPTION OF THE DRAWINGS

For a more complete understanding of the present invention and further advantages thereof, reference is now made to the following Detailed Description, taken in conjunction with the drawings, in which.

DETAILED DESCRIPTION

The frequency orthogonal code division multiplexing (FOCDM) techniques of the present invention may be used in a variety of signal attenuation measurement devices. In the following description, the invention is set forth in the context of a pulse oximeter used to measure blood oxygen saturation or related blood analyte values. As will be described below, the invention has particular advantages in the context of pulse oximetry including allowing for improved noise reduction and oximeter component options. However, while pulse oximetry represents a particularly advantageous application of the present invention, it will be understood that various aspects of the present invention are more broadly applicable in a variety of simultaneous signal attenuation measurement contexts.

Figure 1:
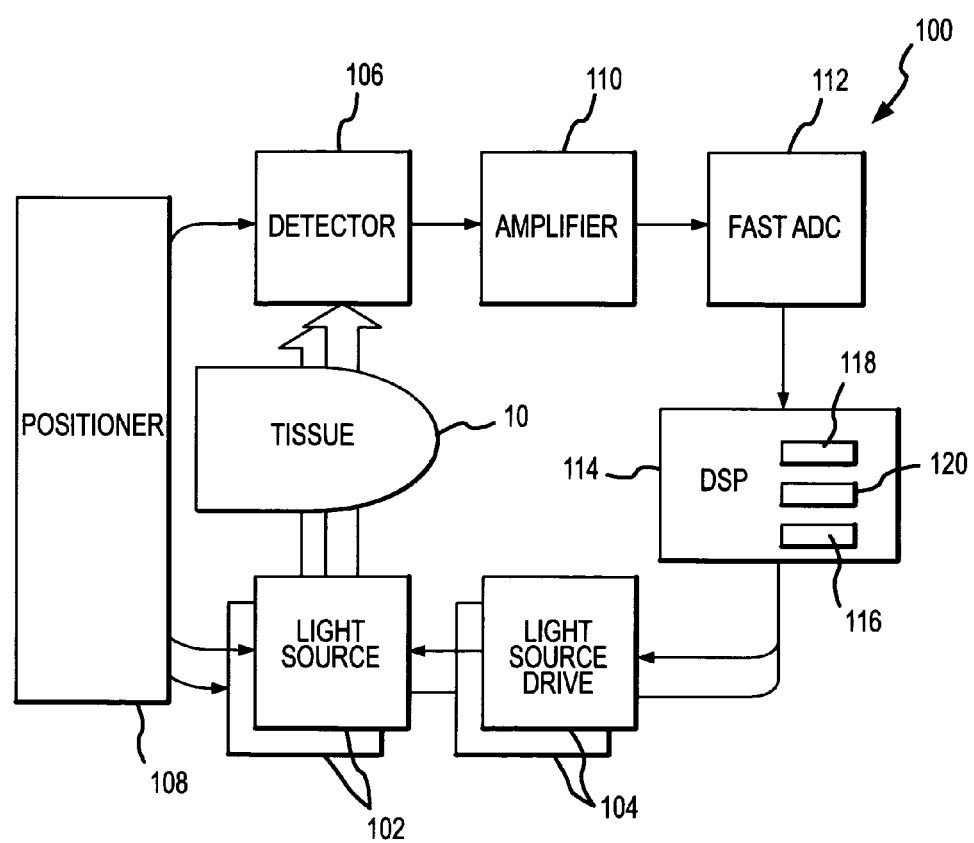
FIG. 1 is a schematic diagram of one embodiment of a pulse oximeter in connection with which the present invention may be implemented.

Referring to FIG. 1, a pulse oximeter in accordance with the present invention is generally identified by the reference numeral 100. The pulse oximeter 100 includes two or more light sources 102 for transmitting optical signals through a tissue site 10 of a patient. In the illustrated embodiment, two light sources 102 are shown. For example, the light sources 102 may comprise a red light emitting diode (LED) or laser diode and an infrared LED or laser diode. The light sources 102 are driven by light source drives 104 in response to drive signals from a digital signal processing (DSP) unit 114. In the illustrated embodiment, as will be described in more detail below, the signals from the light sources 102 are modulated using different code sequences. For example, the source drive 104 associated with the red light source 102 may pulse the red light source in accordance with a first code sequence and the light source drive 104 associated with the infrared light source 102 may pulse the infrared light source 102 in accordance with a second code sequence different from the first code sequence. The code sequences or excitation waveforms, namely the red and IR code sequences, include characteristics of both FDM and CDM techniques. It should be noted that although the following description references "on" and "off" cycles for each of the sources 102 in accordance with their associated code sequences, in reality, the optical signals associated with each source 102 do not define an ideal square wave. For example, substantial photonic energy is emitted even in the "off" state in the case of DC coupled sources. In addition, the intensity transmitted by each of the sources 102 can vary substantially within an "on" cycle. The ability to recognize and address such non-ideal characteristics is an advantage of the present invention.

The optical signals transmitted by the light sources 102 are transmitted through the patient tissue site 10 and impinge upon a detector 106 (e.g., a photo-detector). In this regard, a positioner 108 provides for proper alignment of the sources 102 and the detector 106. Various different types of positioners 108 are available depending, for example, on the tissue site 10 to be irradiated and on the patient (e.g. different positioners 108 may be provided for neonatal and adult patients). One typical type of positioner 108 is provided in the form of a clothespin-like clamp that engages a tissue site 10 comprising a patient's fingertip. When the positioner 108 is engaged on the patient's fingertip, the light sources 102 are positioned on one side of the patient's finger and the detector 106 is positioned on the opposite side in alignment with the light sources so as to receive the optical signals transmitted through the patient's finger and attenuated thereby. It will be appreciated that, in alternative implementations, a reflective pulse oximeter may be employed whereby the sources and detector are located on the same side of the patient's appendage so as to receive optical signals reflected back from the patient tissue site 10.

The detector 106 receives the optical signals transmitted through the patient tissue site 10 and provides an analog signal representative of the received optical signals. In the illustrated embodiment, the detector 106 outputs an analog current signal where the magnitude of the current at any given time is proportional to the cumulative intensity of the received optical signals. The detector signal in the illustrated embodiment is then processed by an amplifier circuit 110. The amplifier circuit 110 may serve a number of functions. First, the illustrated amplifier circuit 110 is operative for converting the input analog current signal from the detector 106 into an analog voltage signal. The amplifier circuit 110 may also be operative for subtracting certain DC and low frequency components from the detector signal. For example, one DC component that may be subtracted from the detector signal relates to photonic energy transmitted by the sources 102 during "dark periods." That is, as noted above, practical source implementations generally transmit a signal of some intensity even during off periods. In addition, low frequency ambient light may be subtracted from the detector signal. The amplifier circuit 110 may also filter out certain high frequency electronic noise and provide other signal processing functionality.

The amplifier circuit 110 outputs an analog voltage signal that is representative of the optical signals from the sources 102. This analog voltage signal is received by a fast A/D converter 112 which samples the analog voltage signal to generate a digital voltage signal which can be processed by the digital signal processing unit 114. In particular, the A/D converter 112 preferably takes multiple digital samples per cycle of each of the sources 102. The sampling rate of the converter 112 should be sufficiently fast to take multiple samples, for example, at least about 3 samples per "on" period of each of the sources 102. Such multiple sampling per cycle allows the oximeter to track the shape of the detector signal, to allow for reduced noise processing of the resulting digital signal and to identify phase components of interest within a signal cycle. Multiple samples per dark period are also obtained. It will thus be appreciated that the values output by the converter 112 are not integrated or aggregate values corresponding to a source cycle period or dark period, but rather, are substantially instantaneous values reflecting the detector signal at a moment within a cycle.

The digital signal processor 114 implements a number of functions. Of particular importance to the present invention, and as will be described in more detail below, the processor 114 includes a demodulation module 118, i.e., the processor 114 executes a variety of demultiplexing software/logic functions including generating or otherwise obtaining a frequency orthogonal coded demultiplexing signal corresponding to each signal component associated with each source (i.e. each channel), processing the composite signal using each of the demultiplexing signals to obtain a set of values reflecting the contribution of each source, and using these value sets to obtain instantaneous intensity related values for each of the channels. The processor 114 also includes a parameter estimation module 120 for calculating blood oxygen saturation or related parameter values using known algorithms.

Implemented within the processor 114 is a code generation module 116 for providing code sequences (the FOCDM codes) that are used to modulate the sources 102 and demultiplex the detector signal. A number of preferred criteria have been identified with respect to the codes employed. First, the codes are preferably selected, relative to one another, in a manner that allows for processing so as to accurately distinguish the contributions of each of the sources. In this regard, the codes may be substantially orthogonal to reduce any interference between the channels corresponding to the two different sources and their wavelengths/spectral composition.

The FOCDM codes may be conceptualized as binary sequences. In the context of the sources it is convenient to conceptualize the code sequence in terms of 0 and 1 bits corresponding to the off or low output state and the on or high output state, respectively. In the case of the demultiplexing signal, the bits are conceptualized as −1 and +1 for mathematical convenience.

The FOCDM codes are used by the light source drives 104 for the respective sources 102 to encode or modulate the signals transmitted by the sources 102. A unique FOCDM code sequence is utilized for each source 102. In the case of a two channel (e.g., red and infrared) pulse oximeter, two separate sequences of FOCDM codes (also referred to herein as FOCDM excitation waveforms) are utilized to modulate the red and infrared sources 102. These may be referred to herein as the red code sequence or excitation waveform and the infrared code sequence or excitation waveform. As may be appreciated, in applications where there are more than two sources to be modulated (e.g. in a four channel pulse oximeter), more than two unique FOCDM excitation waveforms are utilized.

Each FOCDM excitation waveform is comprised of a plurality of code pattern groups (the pattern groups), with each pattern group being comprised of a plurality of code patterns. The code patterns dictate the on and off pulsing operation of each source (i.e., when the sources are turned on and off) and thus are referred to herein as the pulse patterns. As will be described more fully below, the pattern groups comprising multiple pulse patterns achieve evenness and randomization, and the excitation waveforms comprising multiple pattern groups achieve frequency orthogonality.

Preferably, the pulse patterns are band limited. However, the problem of finding band limited pulse patterns is complicated by the need to create symmetrically balanced pulse patterns in time (even functions) that have only one source on at a time, which is a common hardware limitation. In this regard, the pulse patterns excite only a single source at any instant. To achieve symmetry over a full sample period, each pair of pulse patterns is either fully symmetric over the pulse period and the randomization of the pattern group for this source is also symmetric, or the pair is exactly anti-symmetric (odd) and the pattern group randomization is also odd. An example even pair is to turn on the source both early and late in a pulse period or to turn on the source during the middle of the pulse period. An example odd pair is to turn on the source early or to turn on the source late. The shape of each pulse controls the harmonic spectrum, but not the frequency orthogonality. To achieve frequency orthogonal coding, the pattern group is repeated a relatively prime number of times during the whole sample. For a two source system, one sequence is repeated, for example, 2 times, while the other is repeated, for example, 3 times.

Further optimization of the pulse patterns and pattern groups is possible. For instance, although the low pass filtering of the detector will not cause signal separation problems, the slewing of the signal will reduce agreement between the signal and demodulation pattern. The source having slowest response (infrared) can use a pulse pattern that uses less bandwidth and has fewest harmonics, maximizing the amplitude and therefore the signal to noise ratio of the recovered signal. An even pattern turning on the source only in the middle of the pulse period or not at all is such a pulse pattern. Secondly, the randomization is chosen to minimize the energy at any single harmonic, maximizing the whitening of interference.

Figure 2:
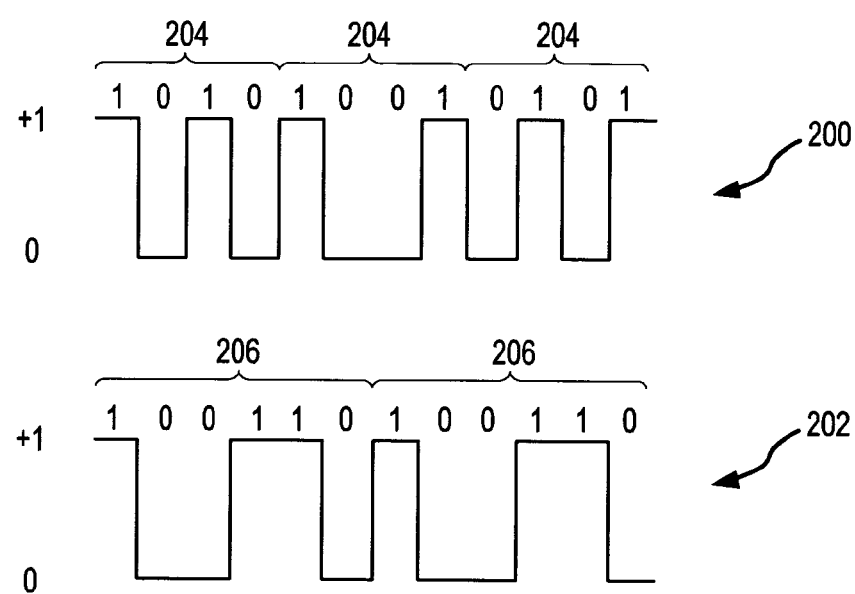
FIG. 2 is a plot showing exemplary pattern groups comprising exemplary infrared and red frequency orthogonal code division multiplexed excitation waveforms.
Figure 3:
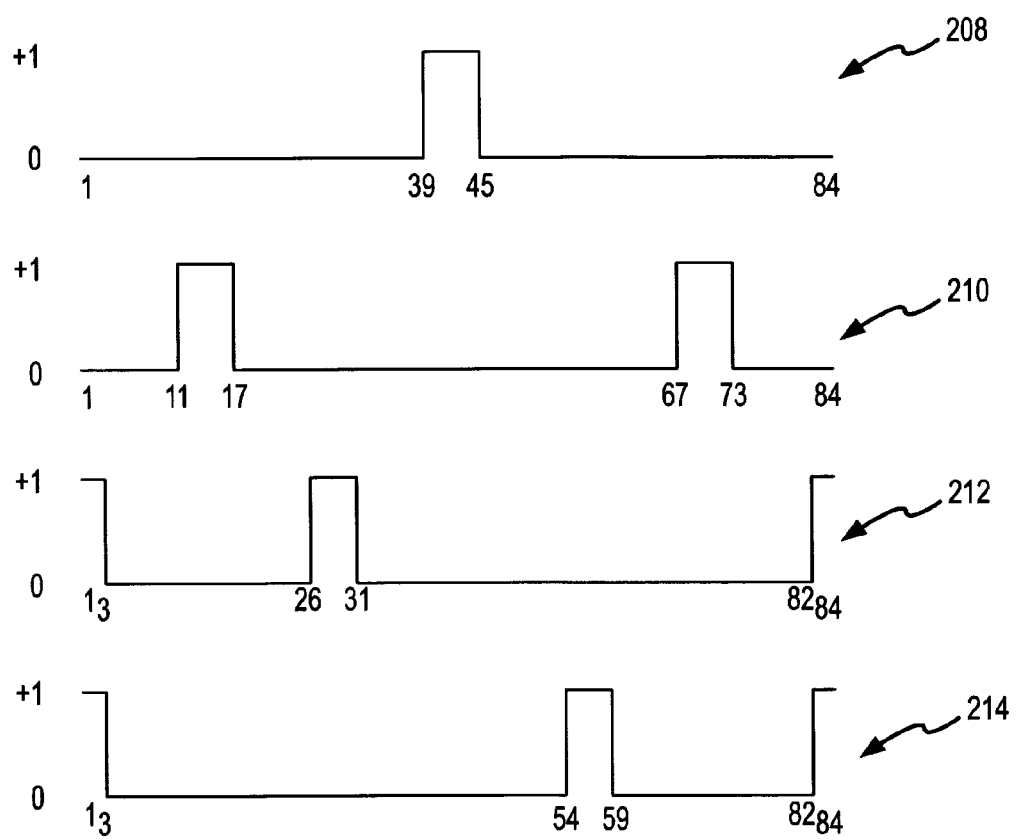
FIG. 3 is a plot showing exemplary infrared and red pulse patterns corresponding to the individual values in the exemplary pattern groups of FIG. 2.

Referring now to FIGS. 2 and 3, the pulse patterns, pattern groups and excitation waveforms may be better understood by reference to particular examples. In this regard, FIG. 2 shows randomly selected values or bits of the pattern groups comprising exemplary first and second frequency orthogonal code division multiplexed excitation waveforms 200, 202 (the infrared and red channel excitation waveforms 200, 202). As is shown in FIG. 2, the infrared channel excitation waveform 200 includes three different infrared channel pattern groups 204, which, in this example are different from one another. In other embodiments, there may be fewer of more than three infrared pattern groups 204 in the infrared channel excitation waveform 200, and in other embodiments the infrared pattern groups 204 may be the same. Each infrared channel pattern group 204 is comprised of 4 random bits, with each bit being either 0 or +1. In other embodiments, each infrared channel pattern group 204 may be comprised of fewer or more random bits. The red channel excitation waveform 202 includes two red channel pattern groups 206, which, in this example, are the same. In other embodiments, there may be fewer or more than two red pattern groups 206 in the red channel excitation waveform 202, and in other embodiments the red pattern groups 206 may be different from each other. Each red channel pattern group 206 is comprised of 6 random bits, with each bit being either 0 or +1. In other embodiments, each red channel pattern group 206 may be comprised of fewer or more random bits.

Each 0 or +1 bit in an infrared channel pattern group 204 corresponds with one of two different infrared channel pulse patterns 208, 210, examples of which are shown in FIG. 3. Each 0 or +1 bit in a red channel pattern group 206 corresponds with one of two different red channel pulse patterns 212, 214, examples of which are also shown in FIG. 3. In this regard, a 0 bit in an infrared channel pattern group 204 corresponds with a first infrared channel pulse pattern 208 (the infrared 0 pulse pattern 208), and a +1 bit in an infrared channel pattern group 204 corresponds with a second infrared channel pulse pattern 210 (the infrared +1 pulse pattern 210). A 0 bit in a red channel pattern group 206 corresponds with a first red channel pulse pattern 212 (the red 0 pulse pattern 212), and a +1 bit in a red channel pattern group 206 corresponds with a second red channel pulse pattern 214 (the red +1 pulse pattern 214). Depending upon whether a particular bit in the infrared and red channel pattern groups 204, 206 is 0 or +1, the infrared and red sources are modulated in accordance with the appropriate corresponding pulse patterns 208–214.

Each of the exemplary pulse patterns 208–214 is of equal length and includes a total of 84 bits. In other embodiments, the pulse patterns 208–214 may include fewer or more bits. In the infrared 0 pulse pattern 208, bits 1 through 38 are 0, bits 39 through 45 are +1 to turn the infrared source on during this portion of the 84-bit pulse period, and bits 46 through 84 are 0. In the infrared +1 pulse pattern 210, bits 1 through 10 are 0, bits 11 through 17 are +1 to turn the infrared source on during this portion of the 84-bit pulse period, bits 18 through 66 are 0, bits 67 through 73 are +1 to turn the infrared source on again during this portion of the 84-bit pulse period, and bits 74 through 84 are 0. The infrared 0 and +1 pulse patterns 208, 210 are an example of an even pair of patterns. In other embodiments, the infrared pulse patterns 208, 210 may be configured to provide an odd pair of pulse patterns. In the red 0 pulse pattern 212, bits 1 through 3 are +1 to turn the red source on during this portion of the 84-bit pulse period, bits 4 through 25 are 0, bits 26 through 31 are +1 to turn the red source on again during this portion of the 84-bit pulse period, bits 32 through 81 are 0, and bits 82 through 84 are +1 to turn the red source on for a third time during this portion of the 84-bit pulse period. In the red +1 pulse pattern 214, bits 1 through 3 are +1 to turn the red source on during this portion of the 84-bit pulse period, bits 4 through 53 are 0, bits 54 through 59 are +1 to turn the red source on again during this portion of the 84-bit pulse period, bits 60 through 82 are 0, and bits 82 through 84 are +1 to turn the red source on for a third time during this portion of the 84-bit pulse period. The red 0 and +1 pulse patterns 212, 214 are an example of and odd pair of pulse patterns. In other embodiments, the red pulse patterns 212, 214 may be configured to provide an even pair of pulse patterns. Preferably, one of the pairs of pulse patterns 208–210 or 212–214 is odd and the other pair of pulse patterns 208–210 or 212–214 is even.

As can be seen from FIG. 3, the portions of the 84-bit pulse period during which the infrared source is on do not coincide with the portions of the 84-bit pulse period during which the red source is on, regardless of which infrared pulse pattern 208, 210 is called for by the current bit of infrared pattern group 204 and which red pulse pattern 212, 214 is called for by the current bit of red pattern group 206. As may be appreciated, the on and off times during the pulse patterns 208–214 may be arranged differently while still achieving the desire of no overlapping on times between either one of the infrared pulse patterns 208, 210 and either one of the red pulse patterns 212, 214.

Figure 4:
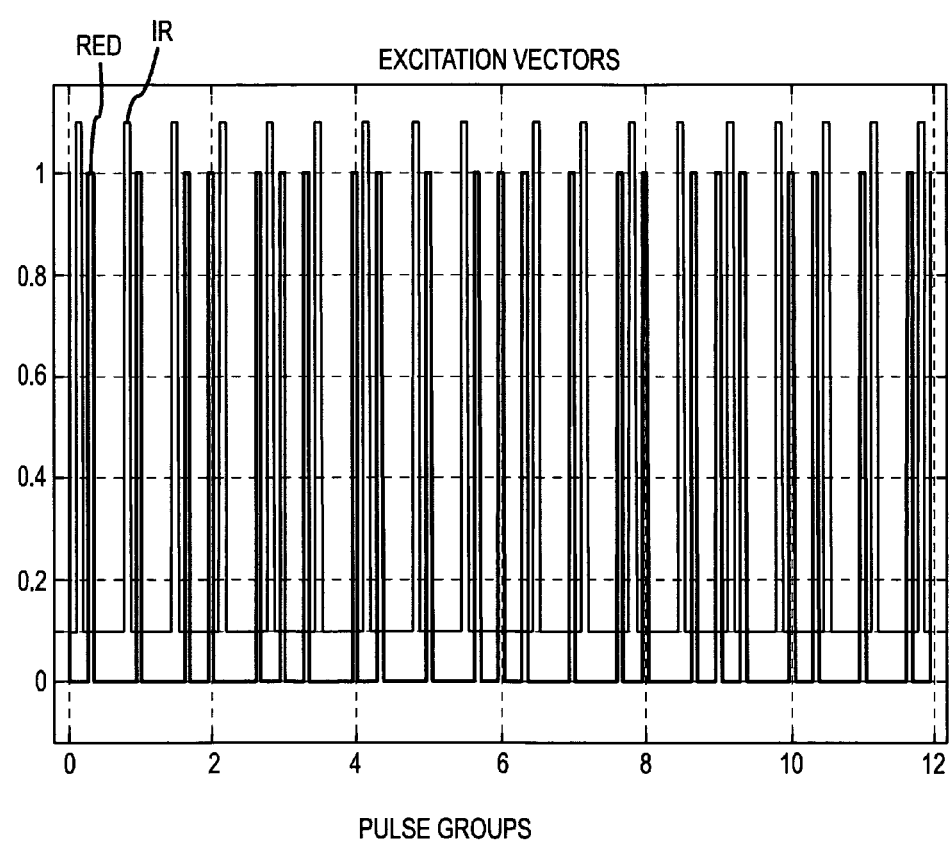
FIG. 4 is a plot showing the on and off times of the exemplary infrared and red frequency orthogonal code division multiplexed excitation waveforms.

With the infrared channel pattern groups 204 and infrared pulse patterns 208, 210 configured as described above, the infrared excitation waveform 200 is thus a series of low (0) and high (+1) values that are 84 bits/pulse pattern×4 bits/pattern group×3 pattern groups=1008-bits long. With the red channel pattern groups 206 and red pulse patterns 212, 214 configured as described above, the red excitation waveform 202 is thus also a series of low (0) and high (+1) values that are 84 bits/pulse pattern×6 bits/pattern group×2 pattern groups=1008-bits long. The 1008-bit long excitation waveforms 200, 202 may be repeated over and over to drive operation of the light sources of the pulse oximeter. FIG. 4 is a plot showing the on (+1) and off (0) times for the exemplary 1008-bit long infrared and red excitation waveforms 200, 202. In FIG. 4, the level of the infrared excitation waveform 200 is shown offset with a value of +0.1 in order to more easily distinguish the infrared on times from the on time portions of the red excitation waveform 202. Although they do not necessarily have to be, typically the levels of the on times will be the same in the infrared and red excitation waveforms 200, 202.

Figure 5:
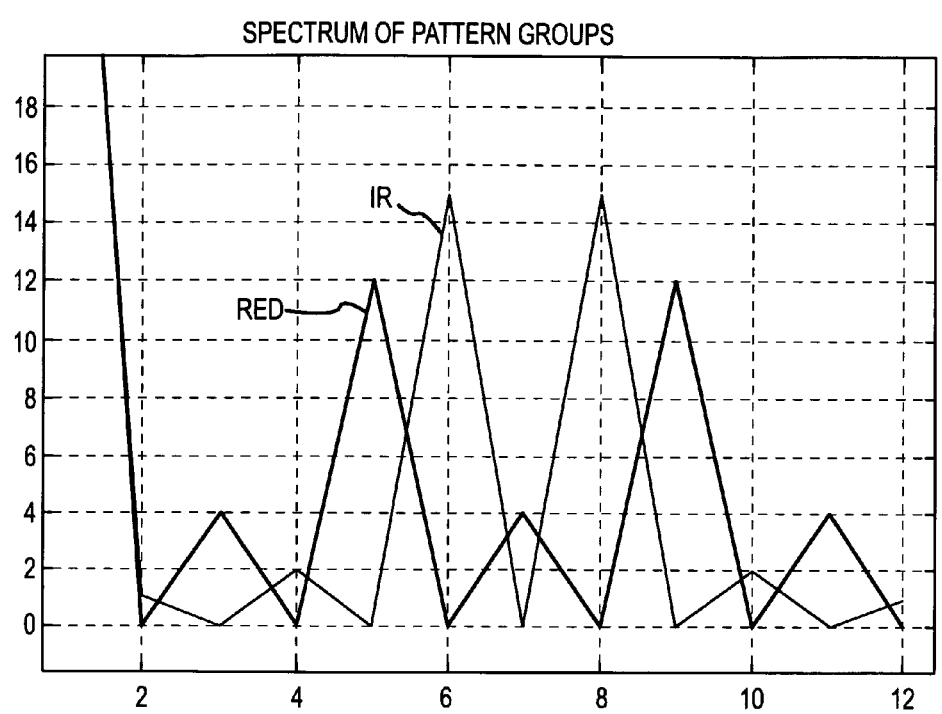
FIG. 5 is a plot of the spectrums of the exemplary infrared and red pattern groups.
Figure 6:
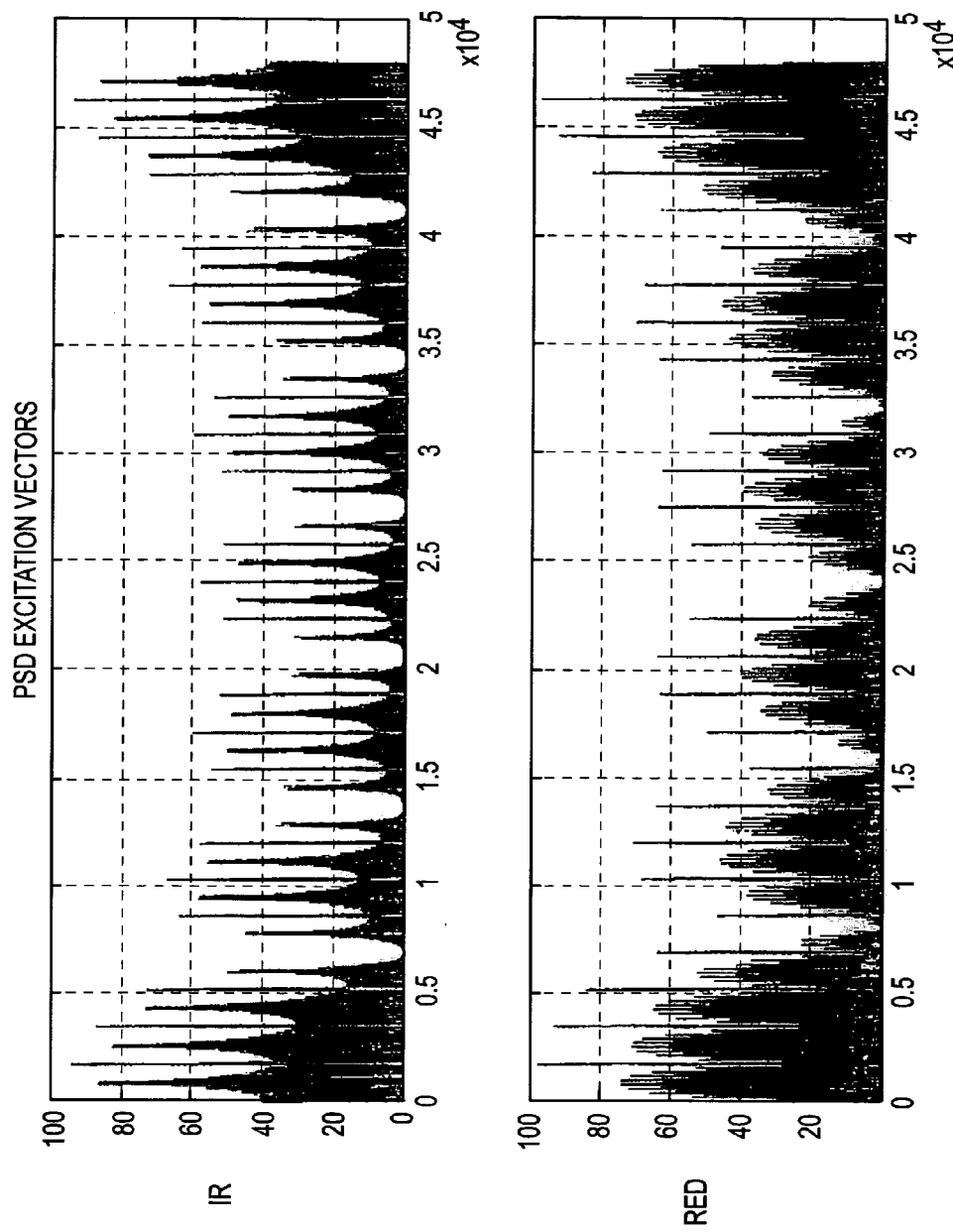
FIG. 6 is a plot of the power spectral densities of the exemplary infrared and red frequency orthogonal code division multiplexed excitation waveforms.
Figure 7:
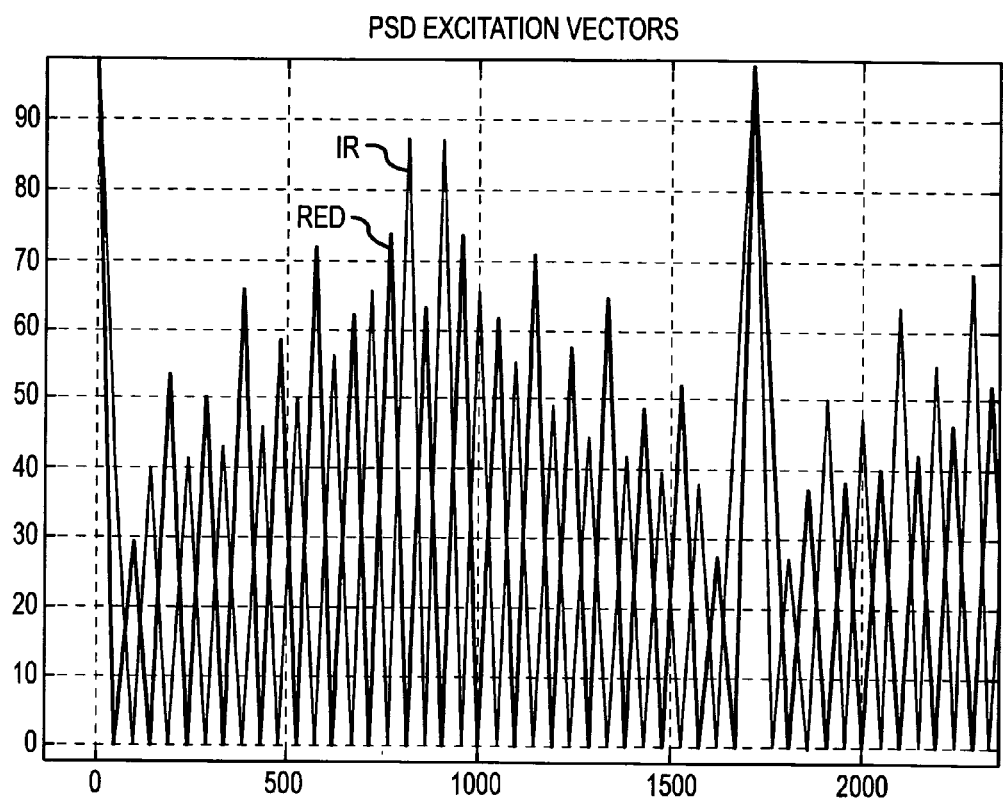
FIG. 7 is a more detailed plot showing the lower frequency portions of the power spectral densities of the exemplary infrared and red frequency orthogonal code division multiplexed excitation waveforms.

As a result of the pseudo-random nature of the individual bits in the pattern groups 204, 206 and their corresponding pulse patterns 208–214 that comprise the excitation waveforms 200, 202, the infrared and red channels are multiplexed in a pseudo-random manner that whitens external noise present in the attenuated infrared and red signal portions of the composite detector signal. As a result of including a different prime number of the pulse groups 204, 206 in the excitation waveforms 200, 202, the infrared and red channels are also multiplexed in a frequency orthogonal manner that achieves good source separation. In this regard, FIG. 5 is a plot of the spectrums for the exemplary random-bit infrared and red pattern groups 204, 206 comprising the excitation waveforms 200, 202. As can be seen from FIG. 5, there is limited overlap in the spectral content of the 12-bit sequences comprising the three infrared pattern groups 204 and the two red pattern groups 206. The frequency orthogonal nature of the excitation waveforms 200, 202 is further seen in FIGS. 6 and 7 which are plots of the power spectral densities for the entire 1008-bit long exemplary infrared and red excitation waveforms, with FIG. 7 showing the lower frequency portions of the power spectral densities in greater detail. As can be seen in FIG. 6 and particularly FIG. 7, there is limited overlap in the spectral content of the infrared and red excitation waveforms 200, 202. Note that there may be some spectral overlap appearing at various harmonics (e.g., the infrared and red spectral peaks appearing at about 1750) due to the fact that the prime numbers (e.g., 2 and 3) share common multiples into which they may be divided an integer number of times (e.g., 6, 12, 18, 24, etc.). However, the demodulation process can easily exclude these overlapping harmonic frequencies since their occurrence is predictable based on the known common multiples of the prime number of infrared pattern groups 204 and the prime number of red pattern groups 206.

Referring again to FIG. 1, the resulting signals transmitted by the sources 102 travel through the patient tissue site 110 in the illustrated embodiment. The signals are received by the detector 106 that provides an electrical detector signal proportional to the received attenuated optical signals. Such a signal may be an analog current signal. In the illustrated embodiment, a single detector 106 receives the signals from both sources 102, thereby reducing components and costs as is desirable, particularly when the detector 106 is provided as part of a disposable or short lifespan probe. Accordingly, the detector signal is a composite signal including contributions from each of the sources 102. The amplifier 110 outputs an analog voltage signal that is representative of the frequency orthogonal code division multiplexed signals from the sources 102. This analog voltage signal is received by the fast A/D converter 112 which samples the analog voltage signal to generate a digital voltage signal which can be processed by the digital signal processing unit 114.

The A/D converter 112 takes multiple digital samples per time period corresponding to the duration of each on or +1 bit in the pulse patterns 208–214. In this regard, the sampling rate of the converter is sufficiently fast to take one or more samples and, more preferably at least about 3 samples and, even more preferably at least about 20 samples per on (+1) or off (0) period of each of the sources 102. Such multiple sampling per cycle allows the oximeter to track the shape of the detector signal, to allow for reduced noise processing of the resulting digital signal, to reduce the required A/D converter word length and to identify phase components of interest within a signal cycle. In one implementation, information regarding the shape of the signal may, for example, be used in filtering the demodulating signal. The FOCDM composite signal may be sampled by the converter, for example, at a frequency of approximately 48,000. Hz. It will thus be appreciated that the values output by the converter 112 are not integrated or aggregate values corresponding to a source cycle period or dark period, but rather, are substantially instantaneous values reflecting the detector signal at a moment within a cycle. The result, in the illustrated embodiment, is that the digitized detector signal as transmitted to the processor 114 is a series of digital values where each digital value corresponds to an intensity of the cumulative signals received by the detector at a given time or short time period.

A demodulation module 118 implemented in the processor 114 demultiplexes the composite digitized detector signal provided thereto by the A/D converter 112. Generally, the demultiplexing process involves processing the composite detector signal using an infrared demultiplexing signal corresponding to the infrared excitation waveform 200 associated with the infrared source 102 to obtain received intensity information for the infrared channel, and processing the composite detector signal using a red demultiplexing signal corresponding to the red excitation waveform 202 associated with the red source 102 to obtain received intensity information for the red channel. The demultiplexing signals are synchronized to the drive signals (e.g., by reference to a common clock or based on a feed forward signal from the analog to digital converter 112) so that corresponding bits of the detector signal and demultiplexing signal are co-processed. The detector signal can then be demultiplexed by taking the bitwise product of the detector signal and demultiplexing signal for a sampling period (e.g., a short portion of a patient's pulse cycle) to obtain a demultiplexed binary sequence. This demultiplexed binary sequence can then be integrated to obtain a value indicative of the intensity of the detected signal portion attributable to the corresponding source 102. Such values form an output that is transmitted to a parameter calculation module 120 implemented within the processor 114 that executes any of various well-known algorithms for determining oxygen saturation or related parameter values based on signal attenuation or the detected intensity values. In this regard, one such algorithm is disclosed in U.S. Pat. No. 5,934,277, the entire disclosure of which is hereby incorporated herein.

While various embodiments of the present invention have been described in detail, further modifications and adaptations of the invention may occur to those skilled in the art. However, it is to be expressly understood that such modifications and adaptations are within the spirit and scope of the present invention.

What is claimed is:

1. An apparatus for use in determining at least one physiological parameter relating to a patient from at least first and second signals transmitted to a patient tissue site and attenuated thereby, said apparatus comprising:
    a source system operative to generate the first and second signals and transmit the first and second signals to the patient tissue site;
    a detector system operative to receive first and second attenuated signals from the patient tissue site corresponding with the first and second signals transmitted to the patient tissue site and provide a composite detector signal based on the first and second attenuated signals; and
    a signal processing device including:
        a code generation module operative to drive the source system to multiplex the first and second signals in accordance with first and second frequency orthogonal code division multiplexed excitation waveforms; and
        a demodulation module operative to demultiplex the composite detector signal using at least one demultiplexing signal said at least one demultiplexing signal including a series of values corresponding with one of the first and second frequency orthogonal code division multiplexed waveforms to obtain demultiplexed information corresponding to each of the first and second attenuated signals, the demultiplexed information being usable in determining the physiological parameter regarding the patient;
        wherein the first frequency orthogonal code division multiplexed excitation waveform comprises a number of first pattern groups, each first pattern group comprising a plurality of randomly selected values wherein each randomly selected value in a first pattern group corresponds with one of a plurality of pulse patterns selected from a first set of pulse patterns, wherein the second frequency orthogonal code division multiplexed excitation waveform comprises a number of second pattern groups, each second pattern group comprising a plurality of randomly selected values wherein each randomly selected value in a second pattern group corresponds with one of a plurality of pulse patterns selected from a second set of pulse patterns, wherein each of the pulse patterns within the first set of pulse patterns and within the second set of pulse patterns is a digital code comprising a series of high and low values, and wherein the high values in each of the pulse patterns within the first set of pulse patterns do not overlap in time with the high values in each of the pulse patterns within the second set of pulse patterns.

2. The apparatus of claim 1 wherein the physiological parameter is at least one of a blood oxygen saturation value and a blood analyte value.

3. The apparatus of claim 1 wherein said source system includes first and second light sources operative to transmit first and second light signals centered at first and second wavelengths.

4. The apparatus of claim 3 wherein the first wavelength is within the infrared portion of the electromagnetic spectrum and the second wavelength is within the red portion of the electromagnetic spectrum.

5. The apparatus of claim 3 wherein the detector system includes a photo-detector.

6. The apparatus of claim 1 wherein the composite detector signal is an analog signal and said detector system includes an analog-to-digital converter operative to convert at least a portion of the detector signal into a series of digital values.

7. The apparatus of claim 6 wherein each of the first and second signals includes high value time periods and low value time periods and said analog-to-digital converter is operative to sample the detector signal multiple times within a time period corresponding to one of said high value and low value time periods of one of the first and second signals.

8. The apparatus of claim 1 wherein said detector system includes an amplifier operative to amplify the detector signal and filter the detector signal to remove one or more selected frequency components.

9. The apparatus of claim 1 wherein said demodulation module demultiplexes the detector signal using a first demultiplexing signal including a series of values corresponding to the first frequency orthogonal code division multiplexed excitation waveform and a second demultiplexing signal including a series of values corresponding to the second frequency orthogonal code division multiplexed excitation waveform signal.

10. The apparatus of claim 1 wherein each of the pulse patterns within the first set of pulse patterns is substantially orthogonal to each of the pulse patterns within the second set of pulse patterns.

11. The apparatus of claim 1 wherein the series of high and low values in each of the pulse patterns within the first and second set of pulse patterns are of equal length.

12. The apparatus of claim 1 wherein the first set of pulse patterns includes two different pulse patterns and wherein the second set of pulse patterns includes two different pulse patterns.

13. The apparatus of claim 1 wherein the number of first pattern groups within the first frequency orthogonal code division multiplexed excitation waveform and the number of second pattern groups within second frequency orthogonal code division multiplexed excitation waveform are prime numbers.

14. The apparatus of claim 13 wherein there is a total of three first pattern groups within the first frequency orthogonal code division multiplexed excitation waveform and a total of two second pattern groups within second frequency orthogonal code division multiplexed excitation waveform, and wherein each first pattern group includes four pulse patterns selected from the first set of pulse patterns and each second pattern group includes six pulse patterns selected from the second set of pulse patterns.

15. An apparatus for use in determining at least one physiological parameter relating to a patient from at least first and second signals transmitted to a patient tissue site and attenuated thereby said apparatus comprising:
 a source system operative to generate the first and second signals and transmit the first and second signals to the patient tissue site;
 a detector system operative to receive first and second attenuated signals from the patient tissue site corresponding with the first and second signals transmitted to the patient tissue site and provide a composite detector signal based on the first and second attenuated signals; and
 a signal processing device including:
  a code generation module operative to drive the source system to multiplex the first and second signals in accordance with first and second frequency orthogonal code division multiplexed excitation waveforms; and
  a demodulation module operative to demultiplex the composite detector signal using at least one demultiplexing signal, said at least one demultiplexing signal including a series of values corresponding with one of the first and second frequency orthogonal code division multiplexed waveforms to obtain demultiplexed information corresponding to each of the first and second attenuated signals, the demultiplexed information being usable in determining the physiological parameter regarding the patient;
 wherein the first frequency orthogonal code division multiplexed excitation waveform comprises a number of first pattern groups, each first pattern group comprising a plurality of randomly selected values wherein each randomly selected value in a first pattern group corresponds with one of a plurality of pulse patterns selected from a first set of pulse patterns, wherein the second frequency orthogonal code division multiplexed excitation waveform comprises a number of second pattern groups, each second pattern group comprising a plurality of randomly selected values wherein each randomly selected value in a second pattern group corresponds with one of a plurality of pulse patterns selected from a second set of pulse patterns, wherein the number of first pattern groups within the first frequency orthogonal code division multiplexed excitation waveform and the number of second pattern groups within second frequency orthogonal code division multiplexed excitation waveform are prime numbers, and wherein there is a total of three first pattern groups within the first frequency orthogonal code division multiplexed excitation waveform and a total of two second pattern groups within second frequency orthogonal code division multiplexed excitation waveform, and wherein each first pattern group includes four pulse patterns selected from the first set of pulse patterns and each second pattern group includes six pulse patterns selected from the second set of pulse patterns.

16. The apparatus of claim 15 wherein the physiological parameter is at least one of a blood oxygen saturation value and a blood analyte value.

17. The apparatus of claim 15 wherein said source system includes first and second light sources operative to transmit first and second light signals centered at first and second wavelengths.

18. The apparatus of claim 17 wherein the first wavelength is within the infrared portion of the electromagnetic spectrum and the second wavelength is within the red portion of the electromagnetic spectrum.

19. The apparatus of claim 17 wherein the detector system includes a photo-detector.

20. The apparatus of claim 15 wherein the composite detector signal is an analog signal and said detector system includes an analog-to-digital converter operative to convert at least a portion of the detector signal into a series of digital values.

21. The apparatus of claim 20 wherein each of the first and second signals includes high value time periods and low value time periods and said analog-to-digital converter is operative to sample the detector signal multiple times within a time period corresponding to one of said high value and low value time periods of one of the first and second signals.

22. The apparatus of claim 15 wherein said detector system includes an amplifier operative to amplify the detector signal and filter the detector signal to remove one or more selected frequency components.

23. The apparatus of claim 15 wherein said demodulation module demultiplexes the detector signal using a first demultiplexing signal including a series of values corresponding to the first frequency orthogonal code division multiplexed excitation waveform and a second demultiplexing signal including a series of values corresponding to the second frequency orthogonal code division multiplexed excitation waveform signal.

24. The apparatus of claim 15 wherein each of the pulse patterns within the first set of pulse patterns is substantially orthogonal to each of the pulse patterns within the second set of pulse patterns.

25. The apparatus of claim 15 wherein each of the pulse patterns within the first set of pulse patterns and within the second set of pulse patterns is a digital code comprising a series of high and low values.

26. The apparatus of claim 25 wherein the series of high and low values in each of the pulse patterns within the first and second set of pulse patterns are of equal length.

27. The apparatus of claim 25 wherein the high values in each of the pulse patterns within the first set of pulse patterns do not overlap in time with the high values in each of the pulse patterns within the second set of pulse patterns.

28. The apparatus of claim 15 wherein the first set of pulse patterns includes two different pulse patterns and wherein the second set of pulse patterns includes two different pulse patterns.

* * * * *